United States Patent [19]
Hancock

[11] Patent Number: 5,511,562
[45] Date of Patent: Apr. 30, 1996

[54] TEMPOROMANDIBULAR JOINT APPLIANCE

[76] Inventor: Raymond R. Hancock, 475 Old Marlton Pike, Marlton, N.J. 08053

[21] Appl. No.: 338,257

[22] Filed: Nov. 14, 1994

[51] Int. Cl.$^6$ ................................................ A61C 5/14
[52] U.S. Cl. ........................ 128/859; 128/861; 128/862
[58] Field of Search ............................... 128/858, 848, 128/859–862; 2/2

[56] References Cited

U.S. PATENT DOCUMENTS

| | | | |
|---|---|---|---|
| 2,827,899 | 3/1958 | Altieri | 128/862 |
| 2,833,278 | 5/1958 | Ross | 128/862 |
| 3,060,935 | 10/1962 | Riddell | 128/861 |
| 3,073,300 | 1/1963 | Berghash | 128/862 |
| 3,236,235 | 2/1966 | Jacobs | 128/862 |
| 3,247,844 | 4/1966 | Berghash | 128/862 |
| 3,319,626 | 5/1967 | Lindsay | 128/861 |
| 3,411,501 | 11/1968 | Greenberg | 128/862 |
| 3,864,832 | 2/1975 | Carlson | 128/862 |
| 4,350,154 | 9/1982 | Feldbau | 128/861 |
| 4,955,393 | 9/1990 | Adell | 128/861 |

*Primary Examiner*—Michael A. Brown
*Attorney, Agent, or Firm*—Norman E. Lehrer; Jeffrey S. Ginsberg

[57] ABSTRACT

A dental appliance for treating temporomandibular joint disorders that includes a U-shaped channel member having an inner side wall and an outer side wall. A plurality of connectors positioned between the inner and outer side walls divide the dental appliance into an upper and lower compartment for receiving a patient's upper and lower teeth, respectively. A pliable material fills the upper and lower compartments so that the grinding or clenching the patient's teeth is prevented and the patient's mandible can be set in a desired position.

5 Claims, 1 Drawing Sheet

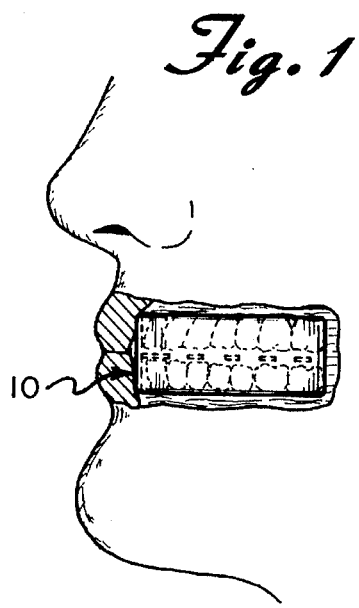
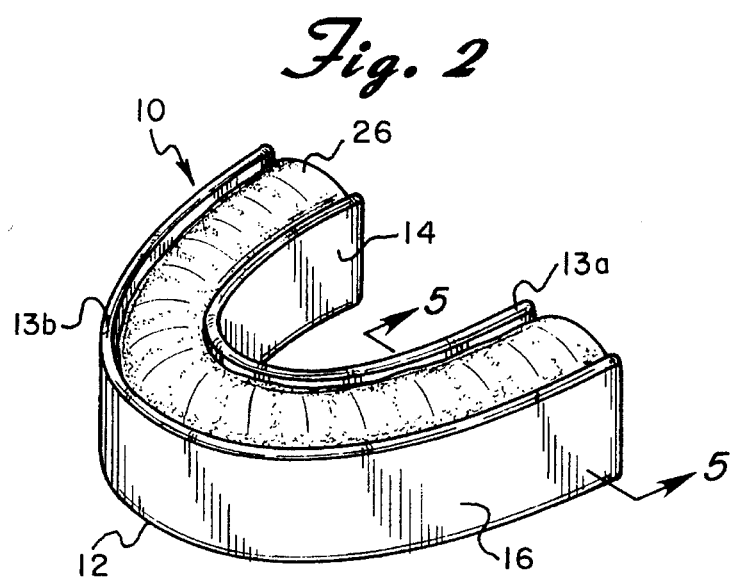
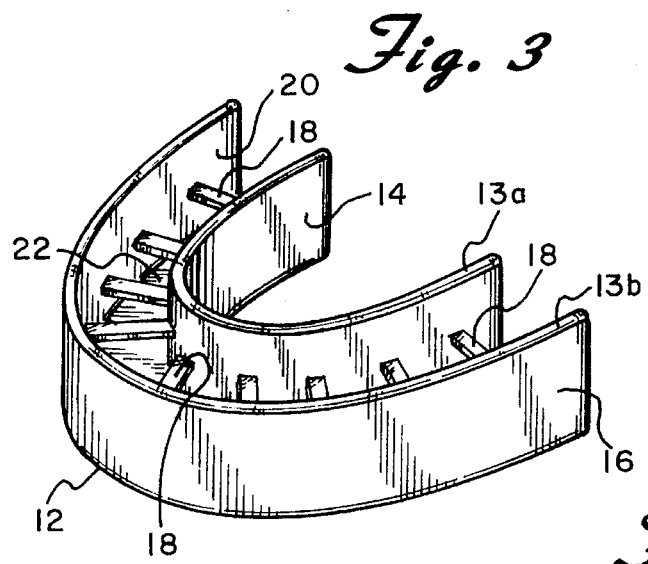
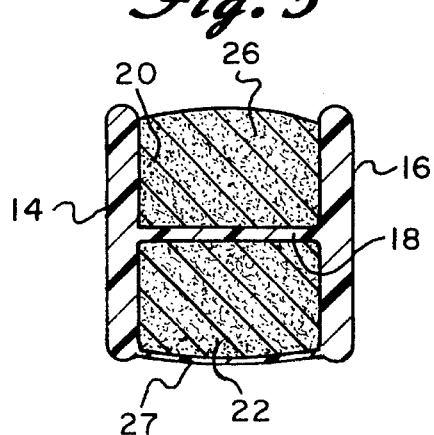
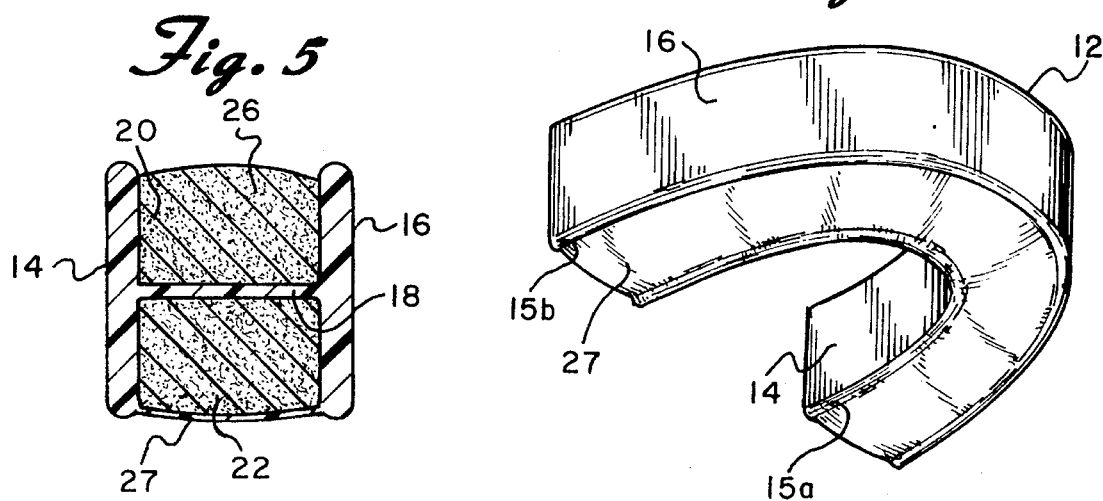

TEMPOROMANDIBULAR JOINT APPLIANCE

BACKGROUND OF THE INVENTION

The present invention is directed toward a dental appliance for treating temporomandibular joint (TMJ) disorders.

The temporomandibular joint or jaw joint is interconnected with the upper neck and back muscles. Improper alignment of the TMJ may lead to a variety of problems. A person suffering from a TMJ disorder, for example, may experience a clicking sound within the joint. Other more severe problems include headache, mandibular muscle fatigue, upper neck pain and upper back pain.

A significant percentage of the population suffers from some degree of temporomandibular dysfunction. Accordingly, an assortment of methods for treating the above mentioned affliction have been developed. A preferred method of treating TMJ disorders involves the use of a device that is inserted into the oral cavity of a patient's mouth.

U.S. Pat. No. 4,568,280 to Ahlin discloses a craniomandibular appliance comprising a thermoplastic dental arch that is inserted into a patient's mouth. The dental arch itself is moldable within the mouth to a fixed configuration so that a predetermined mandibular position can be obtained. In order for the dental arch to be molded it must first be preheated to a temperature above 200° F. This is accomplished by submerging the arch in boiling water. When a sufficient temperature is achieved the dental arch becomes pliable so that when it is inserted into a patient's mouth it can be set in a position to hold the mandible in a desired position. This device is deficient in that it is entirely made of a thermoplastic material so that the entire dental arch becomes malleable when it is heated. Therefore, it may harden in an incorrect form when removed from the heat if the patient's mandible is not properly positioned.

U.S. Pat. No. 3,924,638 to Mann shows a tension reliever intended to be inserted into a patient's mouth. The device disclosed is made of a thermosetting plastic so that it will maintain a rigid form once heated. In one embodiment, the rigid lower surface of the device is lined with a softer material. This softer material, however, is not adapted to form around a user's teeth in such a manner so as to set the mandible in a proper position. Rather, it merely is used to allow the patient to grind his or her teeth without causing any damage thereto.

In addition to the foregoing, U.S. Pat. No. 3,532,091 to Lerman shows a mouthpiece that is suitable for contact sports to protect a user's face and jaws. The mouthpiece comprises a tubular portion and an occlusal portion. The occlusal portion extends inwardly from the tubular portion. In use, the tubular portion of the mouthpiece is positioned between the lips and teeth of the wearer and the occlusal portion is inserted between the occlusal surfaces of the upper and lower teeth. The tubular and occlusal portions each have an internal passage therein. The internal passages are filled with a fluid-like substance which acts as a cushion if the user of the device gets hit in the mouth. In an alternate embodiment, the fluid in the internal passage hardens into a permanent mold of the user's teeth. However, the hardened device is not pliable to provide a comfortable fit in the user's mouth.

Accordingly, there is a need for a dental device that is moldable to fix the patient's mandible in a desired position in order to relieve TMJ disorders and for such a device that is comfortable to wear.

SUMMARY OF THE INVENTION

The present invention is designed to overcome the deficiencies of the prior art discussed above. It is an object of the invention to provide a dental appliance that fixes a patient's mandible in a predetermined position.

It is a further object of the invention to provide a dental appliance that fits comfortably in a user's mouth.

It is yet another object to provide a dental appliance that has a pliable filling in order to prevent the patient from grinding or clenching his or her teeth.

In accordance with the illustrative embodiments and demonstrating features of the present invention there is provided a dental appliance for treating temporomandibular joint disorders that includes a U-shaped channel member having an inner side wall and an outer side wall. A plurality of connectors are positioned between the inner and outer side walls to divide the dental appliance into an upper and lower compartment for receiving a patient's upper and lower teeth, respectively. A pliable material fills the upper and lower compartments so that grinding or clenching of the patient's teeth is prevented and the patient's mandible can be set in a desired position.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a side cross-sectional view of the dental appliance shown inserted in a patient's mouth;

FIG. 2 is a top perspective view of the dental appliance shown with the pliable insert;

FIG. 3 is a top perspective view of the dental appliance shown without the pliable insert;

FIG. 4 is a bottom perspective view of the dental appliance, and

FIG. 5 is a cross-sectional view of the dental appliance taken along lines 5—5 of FIG. 2.

DETAILED DESCRIPTION OF THE DRAWINGS

Referring now to the drawings in detail wherein like reference numerals have been used throughout the various figures to designate like elements, there is shown in the figures a temporomandibular joint appliance constructed in accordance with the principles of the present invention and designated generally as 10.

Referring to FIG. 3, the TMJ appliance 10 includes a U-shaped channel member 12 having an inner side wall 14 and an outer side wall 16. The inner side wall 14 and the outer side wall 16 having top edges 13a and 13b, respectively, and bottom edges 15a and 15b, respectively. In the preferred embodiment, the inner side wall 14 and the outer side wall 16 are between two and three millimeters thick.

The U-shaped member 12 is preferably made of a flexible thermosetting material so that it can comfortably be inserted into a patient's mouth. A plurality of connectors 18 are positioned between the inner side wall 14 and the outer side wall 16. Each connector preferably has a thickness of approximately 0.5 millimeter and is spaced 10 millimeters from adjacent connectors. The connectors 18 divide the dental appliance 10 into an upper compartment 20 and a lower compartment 22 for receiving a patient's upper and lower teeth as shown in FIG. 1.

A pliable material 26 fills the upper compartment 20 and the lower compartment 22 so that the grinding or clenching the patient's teeth is prevented and the patient's mandible can be set in a desired position (see FIGS. 2 and 5). The pliable material 26 can be made of a substance similar to that disclosed in U.S. Pat. No. 4,189,838 to Oliva or any other suitable material. The pliable material 26 is formed to have the property that when the compressive force from the patient's teeth is removed, the material attempts to return to its original shape and size.

A thin flexible plastic shield 27 extends between the bottom edge 15a of inner side wall 14 and the bottom edge 15b of outer side wall 16. The plastic shield 27 acts as a barrier between the patient's lower teeth and the pliable material 26. This prevents the patient's lower teeth from being retained in the pliable material 26. The plastic shield 27 is preferably made of a thermosetting plastic.

To facilitate an understanding of the principles associated with the foregoing apparatus, its operation will now be briefly described. The patient inserts the TMJ appliance 10 into his or her mouth. The patient then bites down on the appliance 10 so that his or her teeth compress the pliable material 26. The patient's upper teeth are supported in the upper compartment 20 while his or her lower teeth are supported in the lower compartment 22 as shown in FIG. 1. The plastic shield 27 prevents the wearer's lower teeth from adhering to the pliable material 26 in the lower compartment 22. The space between the inner side wall 14 and the outer side wall 16 allows the patient's mandible to be adjusted until it is placed in the requisite position. The pliable material 26 then forms around the patient's teeth so that his or her mandible is fixed in this proper position. The appliance also prevents any grinding or clenching of the teeth.

The present invention may be embodied in other specific forms without departing from the spirit or essential attributes thereof and accordingly reference should be made to the appended claims rather than to the foregoing specification as indicating the scope of the invention.

What is claimed is:

1. A dental appliance for treating temporomandibular joint disorders comprising a U-shaped channel member having an inner side wall and an outer side wall, said inner side wall and said outer side wall each having a top edge and a bottom edge, a plurality of connectors positioned between said inner side wall and said outer side wall, said connectors joining said walls together and dividing said dental appliance into an upper compartment and a lower compartment for receiving a patient's upper and lower teeth, respectively, a pliable material filling said upper and lower compartments so that the grinding or clenching of the patient's teeth is prevented and the patient's mandible can be set in a desired position, said pliable material having an unstressed configuration and being compressible upon application of force supplied by the patient's teeth in order to form an accurate impression of the same, said pliable material being capable of substantially returning to said unstressed configuration upon removal of the force supplied by the patient's teeth, and a thin flexible plastic shield extending between said bottom edge of said inner side wall and said bottom edge of said outer side wall for preventing the patient's teeth from being retained in said pliable material.

2. The dental appliance of claim 1 wherein said U-shaped channel member is made of a thermosetting plastic.

3. The dental appliance of claim 1 wherein the U-shaped channel member is made of ethylene vinyl acetate.

4. The dental appliance of claim 1 wherein each of said connectors has a thickness of approximately 0.5 millimeter and is spaced approximately 10 millimeters from adjacent connectors.

5. A dental appliance for treating temporomandibular joint disorders comprising a U-shaped channel member having an inner side wall and an outer side wall, said inner side wall and said outer side wall each having a top edge and a bottom edge, a plurality of connectors positioned between said inner side wall and said outer side wall, said connectors joining said walls together and dividing said dental appliance into an upper compartment and a lower compartment for receiving a patient's upper and lower teeth, respectively, a pliable material filling said upper and lower compartments so that the grinding or clenching of the patient's teeth is prevented and the patient's mandible can be set in a desired position, and a thin flexible plastic shield extending between said bottom edge of said inner side wall and said bottom edge of said outer side wall for preventing the patient's teeth from being retained in said pliable material.

\* \* \* \* \*